United States Patent
Hara (10) Patent No.: US 9,161,689 B2
(45) Date of Patent: Oct. 20, 2015

(54) OPHTHALMOLOGIC PHOTOGRAPHING APPARATUS

(75) Inventor: Hiroshi Hara, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 719 days.

(21) Appl. No.: 12/415,870

(22) Filed: Mar. 31, 2009

(65) Prior Publication Data

US 2009/0251665 A1    Oct. 8, 2009

(30) Foreign Application Priority Data

Apr. 3, 2008   (JP) .................................. 2008-096815

(51) Int. Cl.
  A61B 3/14    (2006.01)
  A61B 3/11    (2006.01)
  A61B 3/00    (2006.01)
  A61B 3/12    (2006.01)

(52) U.S. Cl.
  CPC ............... *A61B 3/112* (2013.01); *A61B 3/0033* (2013.01); *A61B 3/12* (2013.01); *A61B 3/14* (2013.01)

(58) Field of Classification Search
  CPC ........ A61B 3/103; A61B 3/1015; A61B 3/14; A61B 3/12
  USPC .......................................... 351/205–206, 246
  See application file for complete search history.

(56) References Cited

U.S. PATENT DOCUMENTS

| | | | |
|---|---|---|---|
| 5,684,562 A | 11/1997 | Fujieda | |
| 5,790,235 A | 8/1998 | Kirschbaum | |
| 5,980,042 A * | 11/1999 | Hosoi | 351/212 |
| 2002/0099305 A1* | 7/2002 | Fukushima et al. | 600/558 |
| 2006/0077344 A1* | 4/2006 | Kashiwagi et al. | 351/206 |
| 2007/0159598 A1* | 7/2007 | Yancey et al. | 351/206 |
| 2008/0198330 A1* | 8/2008 | Taylor | 351/209 |

FOREIGN PATENT DOCUMENTS

| | | |
|---|---|---|
| EP | 743041 A1 | 11/1996 |
| JP | 02-268730 A | 11/1990 |
| JP | 6-178762 A | 6/1994 |
| JP | 9-140672 A | 6/1997 |
| JP | 05224878 B2 | 7/2013 |
| WO | 2007/013383 A1 | 2/2007 |

* cited by examiner

Primary Examiner — James Greece
(74) Attorney, Agent, or Firm — Canon U.S.A., Inc. IP Division

(57) ABSTRACT

An ophthalmologic photographing apparatus is disclosed which is capable of photographing a predetermined area of a subject's eye. The apparatus includes a light projecting unit configured to project visible light to a subject's eye, a detection unit configured to measure a pupil diameter, which is caused by the light projecting unit, and a control unit configured to determine the amount of change in diameter and to control a photographing operation based on the amount of change determined by the control unit.

6 Claims, 9 Drawing Sheets

| | | |
|---|---|---|
| SETTING OF VARIOUS PARAMETERS | | |
| PARAMETER SET NO. | 1 | F |
| INITIAL AMOUNT OF LIGHT | 100 | A |
| VALUE OF INCREASE IN AMOUNT OF LIGHT OF LIGHT SOURCE | 2 | B |
| MEASUREMENT WAITING TIME | 0.2 | C |
| THRESHOLD FOR AMOUNT OF CHANGE IN PUPIL DIAMETER | 3 | D |
| THRESHOLD FOR AMOUNT OF LIGHT OF LIGHT SOURCE | 10 | E |

OPHTHALMOLOGIC PHOTOGRAPHING APPARATUS

BACKGROUND OF THE INVENTION

1. Field of the Invention

The present invention relates to an ophthalmologic photographing apparatus used in photographing a fundus of a subject's eye at an ophthalmologic clinic.

2. Description of the Related Art

Hitherto, two types of photographing methods, i.e., a mydriatic photographing method and a non-mydriatic photographing method, have been known as methods for photographing fundus images. According to the mydriatic photographing method, fundus photographing is performed by illuminating a fundus of a subject's eye with visible light at both of the time of observing the fundus of the subject's eye and the time of photographing thereof using a mydriatic. According to the non-mydriatic photographing method, fundus photographing is performed without using a mydriatic by illuminating a fundus of a subject's eye with infrared light at the time of observing the fundus of the subject's eye, and illuminating the fundus of the subject's eye with visible light at the time of photographing thereof.

Hitherto, the mydriatic photographing method and the non-mydriatic photographing method have been respectively performed using different apparatuses. Recently, an apparatus capable of performing both of the mydriatic photographing method and the non-mydriatic photographing method has been proposed.

Japanese Patent Application Laid-Open No. 9-140672 discusses a fundus camera in which an infrared filter is detachably arranged in an optical path extending from an illumination optical system, which illuminates a fundus of a subject's eye to be photographed, to the fundus of the subject's eye. An operator of this apparatus switches a mydriatic/non-mydriatic photographing mode selector switch of the fundus camera. Thus, the operator controls attachment/detachment of the infrared filter. Consequently, both of the mydriatic photographing method and the non-mydriatic photographing method can be performed using this single fundus camera.

On the other hand, there have been demands for storing, when the mydriatic photographing method of photographing a fundus of a subject's eye is performed using a mydriatic, information representing a pupil diameter together with image information at the time of photographing the fundus. Techniques for automatically measuring a value of the pupil diameter are discussed as conventional techniques effective for the purpose.

Japanese Patent Application Laid-Open No. 6-178762 discusses a perimeter for photographing a subject's eye using a photographing unit, such as a charge-coupled device (CCD), and for detecting a low-luminance portion on each scanning line while scanning photographed video signals, whereby a value of a pupil diameter can be detected based on a scanning time taken to scan the longest low-luminance portion among the low-luminance portions respectively detected on the scanning lines.

The fundus camera discussed in Japanese Patent Application Laid-Open No. 9-140672 is constructed so as to have the mydriatic/non-mydriatic photographing mode selector switch that an operator operates to select which of a mydriatic photographing mode and a non-mydriatic photographing mode is performed.

When an operation of the fundus camera is transferred to a mydriatic photographing mode, the fundus of a subject's eye is illuminated with visible light when the subject's eye is observed. However, in a case where no mydriatic is used, myosis of the subject's eye is induced. There is a minimum value of a pupil diameter photographable by each ordinary fundus camera. When the myosis of the subject's eye occurs, the pupil diameter thereof becomes less than the minimum pupil diameter. Consequently, the fundus of the subject's eye cannot be photographed.

At that time, it is necessary for photographing the fundus of the subject's eye to wait until the pupil diameter of the subject's eye, which is increased due to natural mydriasis, exceeds the minimum value of the pupil diameter photographable by the fundus camera. A time required by the pupil diameter to exceed the minimum value due to natural mydriasis varies with environment and differences among individual subjects. Thus, such a time may be several minutes. In such a time, the fundus of the subject's eye cannot be photographed. Consequently, efficiency in photographing the fundus is lowered.

Further, Japanese Patent Application Laid-Open No. 6-178762 does not discuss a method for adding the measured pupil diameter to image information. Thus, it is necessary for an operator to manually input the pupil diameter measured at the time of photographing. Accordingly, an operator may add an erroneous value to the image information due to an inputting error and may store the erroneous value added thereto.

SUMMARY OF THE INVENTION

The present invention is directed to an ophthalmologic photographing apparatus capable of determining whether or not a mydriatic has been applied. Advantageously, this information can be used to prevent an operation mode thereof from being, at non-mydriatic photographing, switched to a mydriatic photographing mode due to an operator error. Further, the present invention is also directed to an ophthalmologic photographing apparatus capable of preventing an erroneous value of a pupil diameter measured at the time of photographing from being added to image information and stored.

According to an aspect of the present invention, an ophthalmologic photographing apparatus capable of photographing a predetermined area of a subject's eye includes a light projecting unit configured to project visible light to a subject's eye, a detection unit configured to detect pupil size for the subject's eye, a change in which is caused by a change in the amount of light from the light projecting unit, and a control unit configured to control a photographing operation based on the magnitude of a change in pupil size, detected by the detection unit, as a result of a change in the amount of light from the light projecting unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DETAILED DESCRIPTION OF THE EMBODIMENTS

Various exemplary embodiments, features, and aspects of the invention will be described in detail below with reference to the drawings.

Figure 1:
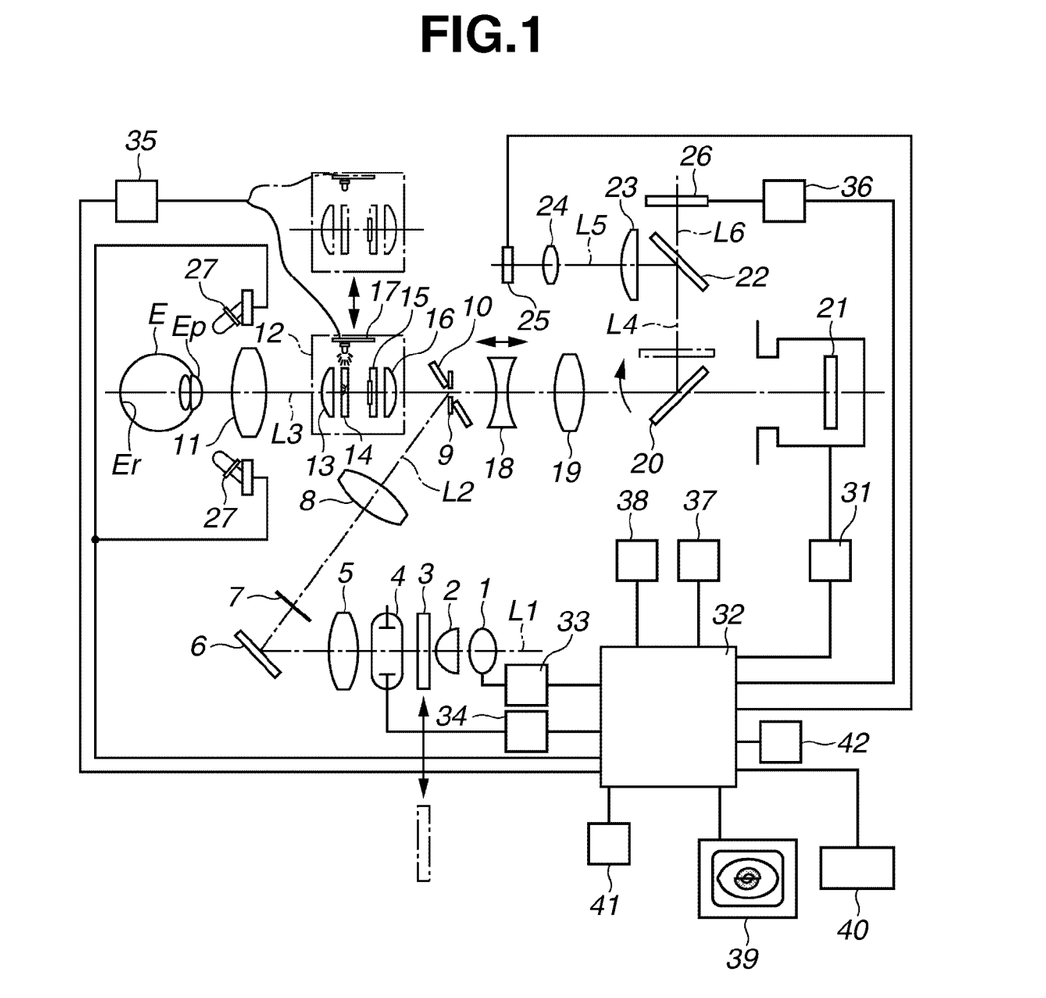
FIG. 1 illustrates a configuration of an ophthalmologic photographing apparatus according to a first exemplary embodiment of the present invention.

FIG. 1 illustrates a configuration of an ophthalmologic photographing apparatus according to a first exemplary embodiment of the present invention. An observation light source 1, such as a halogen lamp, for emitting stationary light, a condenser lens 2, a filter 3 for transmitting infrared light and for cutting off visible light, a photographing light projecting light source 4, such as a flash unit, for projecting photographing light, a lens 5, and a mirror 6 are arranged on an optical axis L1. On the other hand, a ring diaphragm 7 having a ring-like opening, a relay lens 8, and a perforated mirror 10 having a central part opening, in which a diaphragm 9 is disposed, are sequentially arranged on an optical axis L2 extending in a reflecting direction of the mirror 6.

The filter 3, functioning as a wavelength range switching unit, is placed differently depending upon which of the mydriatic photographing mode and the non-mydriatic photographing mode a photographing mode of the ophthalmologic photographing apparatus is. In a case where the photographing mode of the ophthalmologic photographing apparatus is the non-mydriatic photographing mode, invisible range wavelength infrared light is irradiated onto the subject's eye E. Thus, the filter 3 is placed on the optical axis L1. In a case where the photographing mode of the ophthalmologic photographing apparatus is the mydriatic photographing mode, visible range wavelength light is irradiated onto the subject's eye E. Thus, the filter 3 is moved out of the optical axis L1, as indicated by an arrow.

An objective lens 11 is placed on an optical axis L3 extending in a reflecting direction of the perforated mirror 10 so as to be opposed to the subject's eye E. An anterior eye observation optical system 12 is removably placed on the optical axis L3 between the objective lens 11 and the perforated mirror 10. A lens 13, a target member 14, a prism 15 having an image splitting prism provided at a central portion thereof, and a lens 16 are arranged in the anterior eye observation optical system 12. A target illuminating light source 17 for illuminating the target member 14 from a side is placed in the vicinity of the target member 14. The prism 15 is located so as to be substantially conjugated with an anterior eye portion $E_p$ of the subject's eye E with respect to the objective lens 11 and the lens 13 when an operating distance between the subject's eye E and the objective lens 11 is appropriate. These members, constituting the anterior eye observation optical system 12, can be removably and integrally inserted onto the optical axis L3.

A focusing lens 18, a photographing lens 19, a flip-up mirror 20, and a still image sensor 21 are sequentially arranged in rear of the perforated mirror 10. The focusing lens 18 is moved on the optical axis L3 in order to adjust focusing. The flip-up mirror 20 serves to switch between a photographing optical system and an observation optical system. A dichroic mirror 22 for reflecting infrared light and for transmitting visible light is placed on an optical axis L4 extending in a reflecting direction of the flip-up mirror 20.

A field lens 23, a lens 24, and an observation image sensor 25 are sequentially arranged on an optical axis L5 extending in a reflecting direction of the dichroic mirror 22.

A fundus observation fixation target projecting unit 26 including a liquid crystal display panel and a backlight is located on an optical axis L6 in a transmitting direction of the dichroic mirror 22 so as to be optically conjugated with the still image sensor 21. The fundus observation fixation target projecting unit 26 projects the fixation target onto a predetermined area of a fundus portion $E_r$ of the subject's eye E in order to draw a line of sight of the subject's eye. In addition, a plurality of anterior eye illuminating light sources 27 directed to the subject's eye E are located in the neighborhood of the objective lens 11.

An output of the still image sensor 21 is displayed on a monitor 39 via an image processing unit 31 and a control unit 32. On the other hand, an output of the observation image sensor 25 is displayed on the monitor 39 via the control unit 32. The control unit 32 controls the observation light source 1 via an observation light source control unit 33. Further, the control unit 32 controls the photographing light projecting light source 4 via a photographing light source control unit 34. Furthermore, the control unit 32 controls the target illuminating light source 17 of the anterior eye observation optical system 12 via the anterior eye observation fixation target light source control unit 35. The control unit 32 controls the fundus observation fixation target projecting unit 26 via a fundus observation fixation target light source control unit 36. Further, the control unit 32 controls the anterior eye illuminating light sources 27.

A work memory 37, an image memory 38, a monitor 39, a keyboard 40, an observation region selecting switch 41, and a photographing switch 42 are connected to the control unit 32. The control unit 32 includes controllers, such as a central processing unit (CPU), and computer-readable memories, such as a read-only memory (ROM), which store programs for operating the ophthalmologic photographic apparatus. Incidentally, the control unit 32 can be constructed integrally with hardware, such as the observation light source control unit 33, the photographing light source control unit 34, the anterior eye observation fixation target light source control unit 35, and the fundus observation fixation target light source control unit 36.

Figure 2:
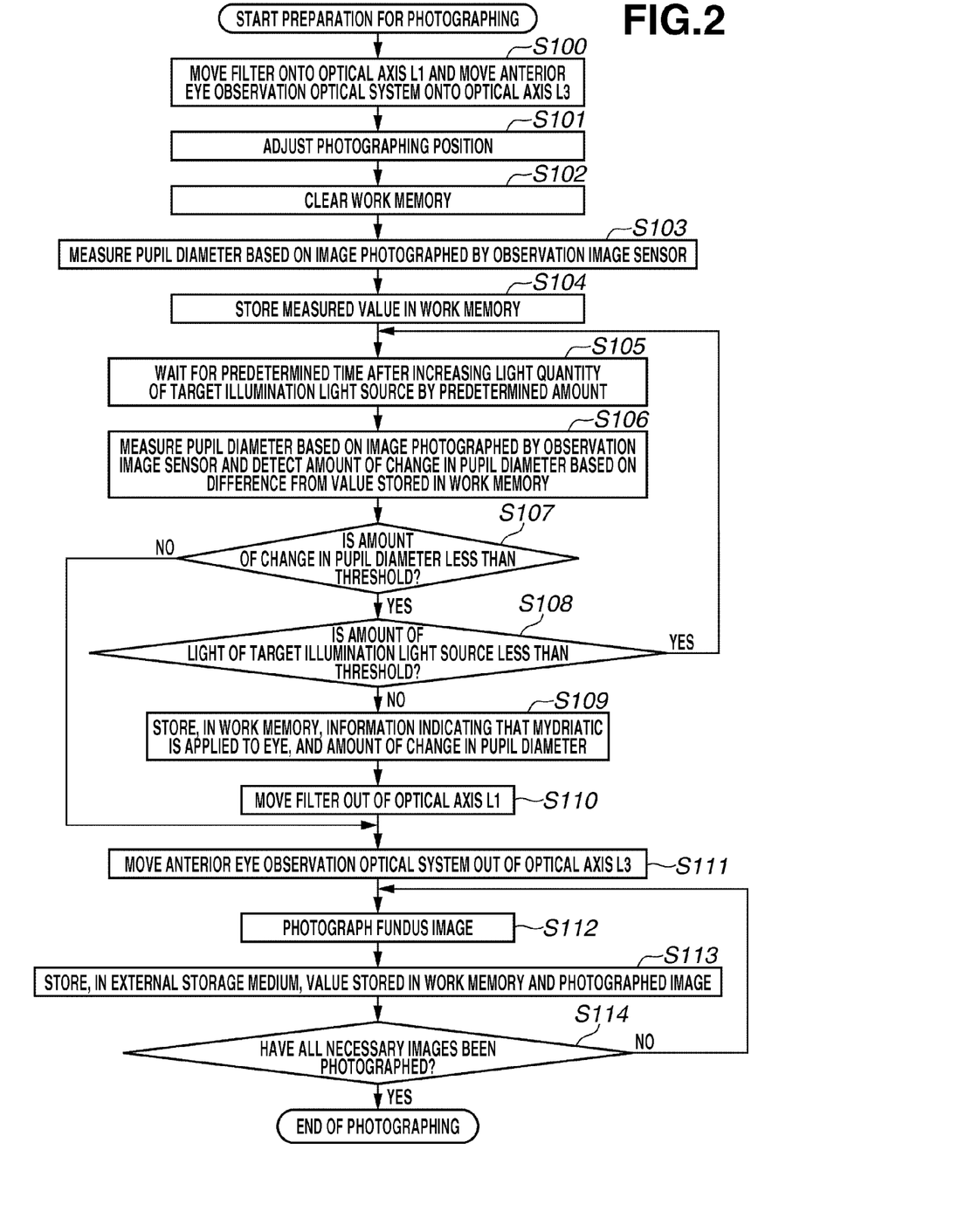
FIG. 2 illustrates a flow of an operation of the ophthalmologic photographing apparatus according to the first exemplary embodiment of the present invention.

FIG. 2 illustrates a flow of an operation performed by the control unit 32 of the ophthalmologic photographing apparatus according to the present embodiment.

In step S100, if the preparation for photographing is started, the control unit 32 performs a control process for moving the filter 3 onto the optical axis L1. Then, if an operation caused due to the observation region selecting switch 41 is detected, the control unit 32 performs a control process for inserting the anterior eye observation optical system 12 onto the optical axis L3. Thus, infrared light for observing the subject's eye E is projected thereonto. In addition, a photographing position can be adjusted using the anterior eye observation optical system 12.

In step S101, the photographing position is adjusted by an operator. First, the control unit 32 turns on the anterior eye illuminating light source 27. Then, the control unit 32 turns on the target illuminating light source 17 at a predetermined amount of light via the anterior eye observation fixation target light source control unit 35. A light flux projected by the target illuminating light source 17 reaches the subject's eye E through the optical axis L3. The target illuminating light source 17 acts as a visible light projecting unit for projecting visible light onto the subject's eye E. The target illuminating light source 17 projects light to the subject's eye E in association with change in the amount of light projected thereto by adjusting an amount of light from the target illuminating light source 17.

Light emitted from the anterior eye illuminating light source 27 illuminates the anterior eye portion $E_p$ of the subject's eye E. A light flux, which is reflection-scattered by the subject's eye E, is reflected by the flip-up mirror 20 in the direction of the optical axis L4 via the objective lens 11, the anterior eye observation optical system 12, the photographing diaphragm 9, the focusing lens 18, and the photographing lens 19. The reflected light is formed into an image on the observation image sensor 25 by the field lens 23 and the lens 18 after being reflected by the dichroic mirror 22 in the direction of the optical axis L5. Then, the image photographed by the observation image sensor 25 is displayed on the monitor 39 by the control unit 32.

An operator roughly adjusts the photographing position by manipulating an operating lever (not shown), while observing the image of the anterior eye portion Ep of the subject's eye E, which is displayed on the monitor 39.

In step S102, the control unit 32 clears the work memory 37. The work memory 37 is used for temporarily storing information that is acquired by the fundus camera and that represents measured values and amounts of change of the pupil diameter of the subject's eye E, the presence/absence of the application of a mydriatic to the subject's eye E, and the presence/absence of a myosis of the subject's eye E.

In step S103, the control unit 32 measures the pupil diameter based on an image photographed by the observation image sensor 25. The measurement of the pupil diameter is performed by transmitting the image photographed by the observation image sensor 25 to the control unit 32 and using a method of performing a method discussed in Japanese Patent Application Laid-Open No. 6-178762 or a method of obtaining the pupil diameter from the area of a pupil by approximating the pupil with a circle.

The term "diameter" is used throughout the description for the sake of convenience. However, it is noted that any measurement of the pupil size, which is indicative of the degree to which a pupil is dilated, can be utilized. Consequently, the term "diameter" should not be considered to limit the scope of the invention by excluding other measurements of pupil size or degree of dilation.

In step S104, the control unit 32 causes the work memory 37 to store the measured value of the pupil diameter.

In step S105, the control unit 32 increases an amount of light from the target illuminating light source 17 by a preliminarily set amount via the anterior eye observation fixation target light source control unit 35. Subsequently, the control unit 32 waits for a predetermined time.

In step S106, the control unit 32 measures the pupil diameter by performing a procedure similar to that performed in step S103. Subsequently, the control unit 32 detects an amount of change in the pupil diameter by subtracting a measured value of the pupil diameter, which is measured after the amount of light is increased, from the measured value of the pupil diameter that is stored in the work memory 37 in step S104 and that is measured before the amount of light is increased.

In step S107, the control unit 32 determines whether an amount of change in the pupil diameter, which is detected in step S106, is less than a threshold. If the amount of change in the pupil diameter is equal to or more than the threshold (NO in step S107), the control unit 32 determines that the amount of change in the pupil diameter is large, and that non-mydriatic photographing is being performed. Thus, the control unit 32 proceeds to step S111 while the filter 3 is kept inserted onto the optical axis L1.

In step S108, if the control unit 32 determines based on a result of comparison made in step S107 that the amount of change in the pupil diameter is less than the threshold, the control unit 32 determines whether the amount of change is small because the amount of light from the target illuminating light source 17 is less than a threshold. If the control unit 32 determines based on a result of comparison that the amount of light from the target illuminating light source 17 is less than the threshold, the control unit 32 performs processing to be performed in step S105 or later again.

In step S109, if it is determined based on a result of the comparison made in step S108 that the amount of light is equal to or larger than the threshold, the control unit 32 determines that mydriatic photographing is being performed by applying a mydriatic to the subject's eye E. Thus, the control unit 32 causes the work memory 37 to store information indicating that mydriatic photographing is being performed, and information representing the amount of change in the pupil diameter acquired in step S106.

In step S110, the control unit 32 performs a control process for moving the filter 3 out of the optical axis L1. A light flux of light for observing the subject's eye E is set by the movement of the filter 3 to be that of visible light. This enables observing a color image of the subject's eye E.

In step S111, the control unit 32 performs a control process for moving the anterior eye observation optical system 12 out of the optical axis L3 via the anterior eye fixation target light source control unit 35. This movement of the anterior eye observation optical system 12 changes an image to be formed onto the still image sensor 21 or the observation image sensor 25 from an image of the anterior eye portion $E_p$ of the subject's eye E to an image of the fundus portion $E_r$ thereof. Thus, a fundus image can be photographed.

In step S112, the control unit 32 performs a control process for projecting an image of the fundus observation fixation target projecting unit 26 onto the fundus portion $E_r$ via the fundus observation fixation target light source control unit 36. Thus, the subject's eye E is caused to perform fixation. The fundus portion $E_r$ is observed with visible light while the mydriatic photographing thereof is performed. On the other hand, while the non-mydriatic photographing of the fundus portion $E_r$ is performed, the fundus portion $E_r$ is observed with infrared light using the filter 3. Then, if the control unit 32 detects an operation of the photographing switch 42, the control unit 32 instantaneously turns on the photographing light projecting light source 4. Thus, the photographing of a color fundus image is performed by the control unit 32 using the still image sensor 21.

In step S113, the control unit 32 causes an external storage medium (not shown) to store information representing the photographed image and the information stored in the work memory 37.

In step S114, the control unit 32 determines whether all necessary images have been photographed. If there is an image that is not photographed, the control unit 32 performs processing to be performed in step S112 or later again. Incidentally, fixed values can be used as values of the amount of light to be used for the adjustment of the position in step S101, the predetermined amount and the waiting time in step S105, and the thresholds used in steps S107 and S108. Alternatively, the parameters can be selected from a combination of a plurality of values. More alternatively, the parameters can be input from the keyboard 40 before the subject's eye E is photographed.

Figure 3:
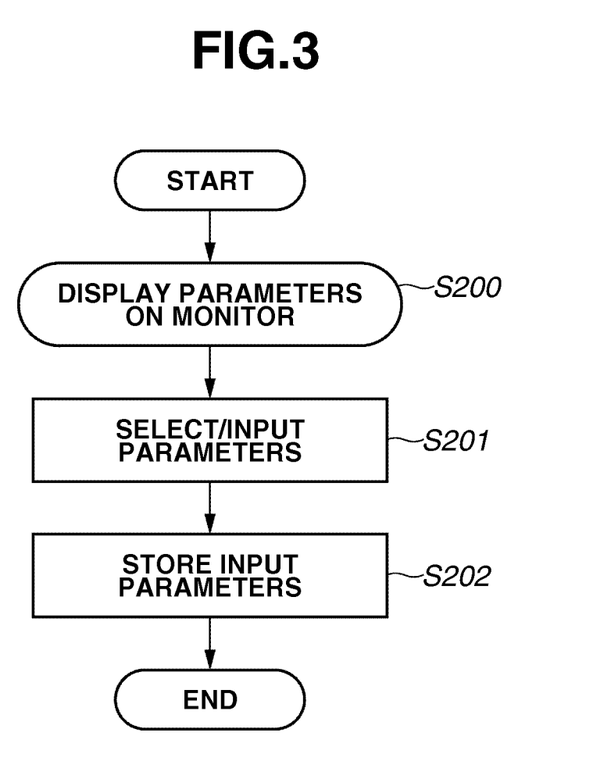
FIG. 3 illustrates a flow of an operation of selecting and inputting parameters in the ophthalmologic photographing apparatus according to the first exemplary embodiment of the present invention.
Figure 4:
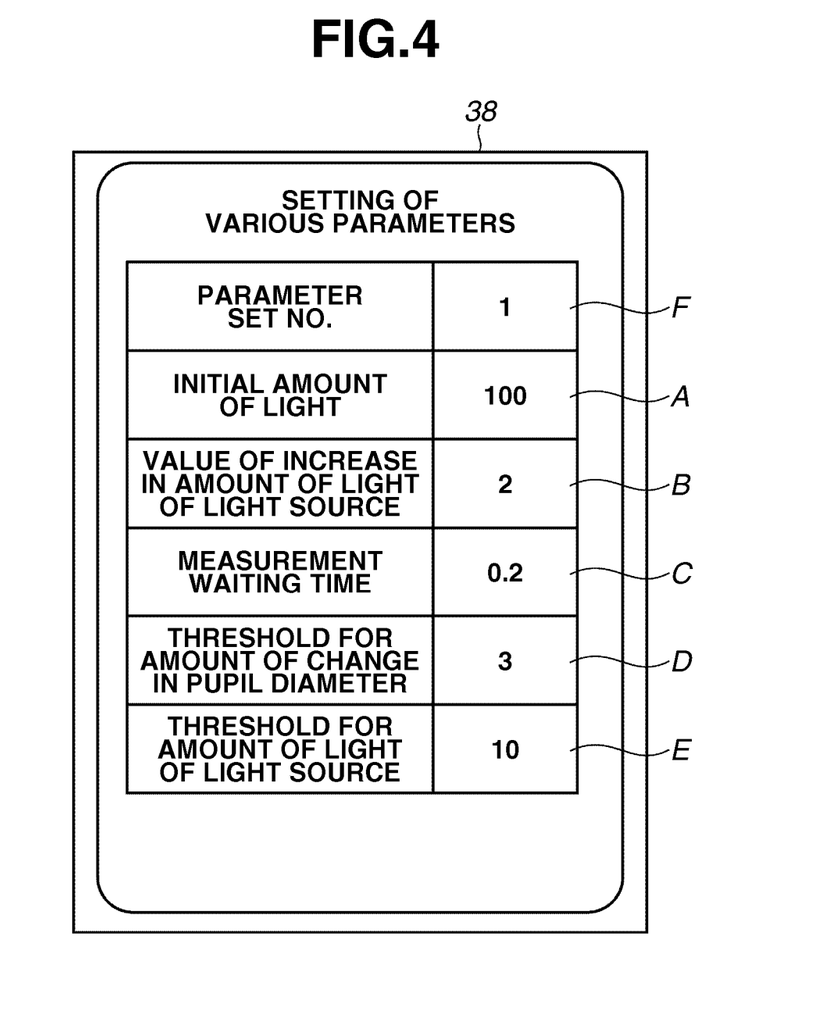
FIG. 4 illustrates a parameter set displayed by a monitor of the ophthalmologic photographing apparatus according to the first exemplary embodiment of the present invention in the operation of selecting and inputting parameters.

FIG. 3 illustrates a flow of an operation of selecting the parameters. FIG. 4 illustrates a parameter set displayed by the monitor 39 when the operation of selecting and inputting the parameters is performed.

In step S200, if the setting of the parameters is started, the control unit 32 performs a process for displaying currently set values of the parameters on the monitor 39 in a format illustrated in FIG. 4.

As illustrated in FIG. 4, the parameter set includes an initial amount of light A of the target illuminating light source 17 at the time of adjusting the position, a value B of an increase in the amount of light from the target illuminating light source 17 in a case where the amount of light from the target illuminating light source 17 is increased, a measurement waiting time C, a threshold D for an amount of change in the pupil diameter, and a threshold E for an amount of light from the target illuminating light source 17. A parameter set No. F is used for grouping and managing the set values.

In step S201, an operator selects or inputs the parameters displayed on the monitor 39 using the keyboard 40. The parameters are selected from a plurality of groups respectively constituted by combinations of the set values of the parameters A through E by changing the value of the parameter set No. F illustrated in FIG. 4. In a case where the selected parameters are changed or input, the value of the parameter to be input is directly input from the keyboard 40. The control unit 32 acquires information representing the input parameter.

In step S202, the control unit 32 finishes setting of the parameters by storing the input parameters. The input parameter is stored in response to, e.g., detection of an input operation of a specific key of the keyboard 40. The setting of the parameters is performed before the preparation for photographing is performed. Thus, the amount A of light used in step S101, the predetermined amount B and the waiting time C used in step S104, and the threshold D used for comparison in step S108, and the threshold E used for comparison in step S109 can be changed.

Figure 5:
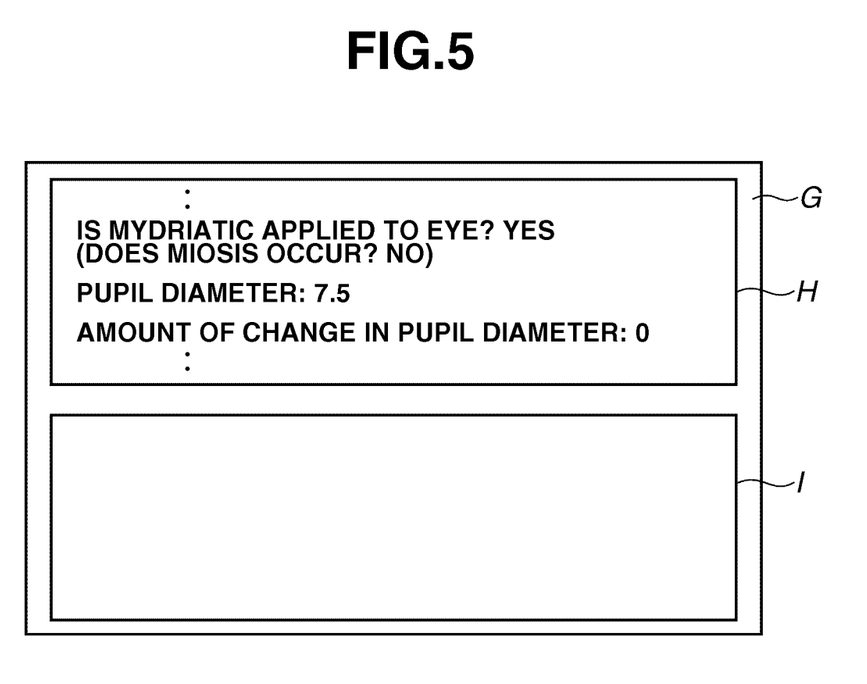
FIG. 5 illustrates a format of a file to be stored in an external storage medium.

FIG. 5 illustrates a format of each file G of content information and image information stored in the work memory 37, which are to be stored in an external storage medium. The file G stored in the work memory 37 includes header information H and image information I. Information indicating that a mydriatic is applied to the subject's eye E, information representing a measured value of the pupil diameter, and information representing an amount of change in the pupil diameter to be stored in the work memory 37 are stored as a part of the header information H.

In a case where information indicating that a mydriatic is applied to the subject's eye E, information representing a measured value of the pupil diameter, and information representing an amount of change in the pupil diameter are not stored in the work memory 37, the control unit 32 causes the work memory 37 to store information indicating that no mydriatic is applied to the subject's eye E, as the header information H. In this case, the control unit 32 does not cause the work memory 37 to store information representing an amount of change in the pupil diameter. Incidentally, the cause for making the amount of change in the pupil diameter less than the threshold is not always the application of a mydriatic to the subject's eye E. Accordingly, information indicating that a mydriatic is applied to the subject's eye E can be recorded as information representing the presence/absence of occurrence of myosis.

Thus, the ophthalmologic photographing apparatus according to the first exemplary embodiment includes a unit configured to project visible range wavelength light, whose amount is variable, onto the subject's eye E using the target illuminating light source 17, and a unit configured to detect an amount of change in the pupil diameter of the subject's eye E, which is caused in association with the projection of the visible range wavelength light. Further, observation light used for observing the subject's eye E is changed, based on the amount or magnitude of the change in the pupil diameter, to the visible wavelength range or to the infrared wavelength range. Consequently, observation visible light can be prevented from being irradiated onto the pupil Ep in the non-mydriatic photographic mode.

The ophthalmologic photographing apparatus according to the first exemplary embodiment further includes a unit configured to measure the pupil diameter of the subject's eye E. Both of information representing the measured pupil diameter and information indicating that a mydriatic is applied to the subject's eye E are stored together with information representing the photographed image. This eliminates necessity for manually inputting a measured value. Occurrence of an inputting error can be prevented.

According to the first exemplary embodiment, the ophthalmologic photographing apparatus operates so as to change the photographing method by automatically determining whether a mydriatic is applied to the subject's eye E. Even in a case where an operator forgets to apply a mydriatic to the subject's eye E in the mydriatic photographic mode, the ophthalmologic photographing apparatus can photograph the fundus of the subject's eye E. Accordingly, there is a fear that after the fundus of subject's eye E is photographed, the operator may notice that the operator has forgotten to apply a mydriatic thereto.

Consequently, according to the procedure described in the description of the first exemplary embodiment, the ophthalmologic photographing apparatus can operate so as to detect the amount of change in the pupil diameter of the subject's eye E, to give notice to an operator based on the amount of change in the pupil diameter, and to stop a photographing operation.

Figure 6:
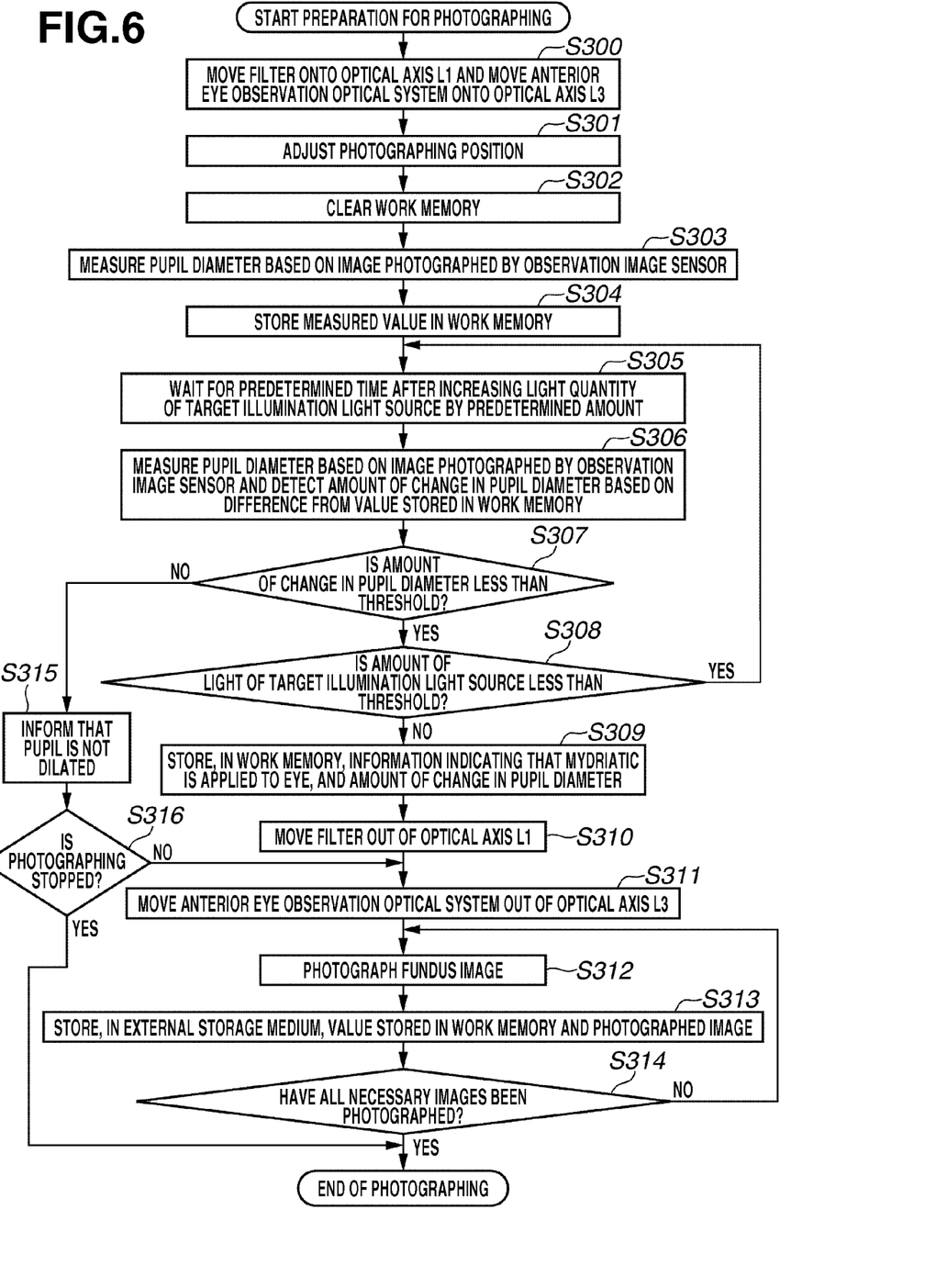
FIG. 6 illustrates a flow of an operation of an ophthalmologic photographing apparatus according to a second exemplary embodiment of the present invention.

FIG. 6 illustrates a flow of an operation of an ophthalmologic photographing apparatus according to a second exemplary embodiment of the present invention, which has a configuration illustrated in FIG. 1 and is adapted to give notice to an operator based on the amount of change in the pupil diameter, and to stop a photographing operation. The operation illustrated in FIG. 6 is performed under the control of the control unit 32 of the ophthalmologic photographing apparatus. Incidentally, processing to be performed in each of steps S300 through S314 is similar to that to be performed in associated one of steps S100 through S114.

In step S300, if the preparation for photographing is started, the control unit 32 performs a control process for moving the filter 3 onto the optical axis L1. Then, the control unit 32 performs a control process for inserting the anterior eye observation optical system 12 onto the optical axis L3. Thus, infrared light for observing the subject's eye E is projected there onto. In addition, a photographing position can be adjusted using the anterior eye observation optical system 12.

In step S301, the photographing position is adjusted by an operator. This adjustment of the photographing position is performed by a procedure similar to that performed in step S101 illustrated in FIG. 2.

In step S302, the control unit 32 clears the work memory 37.

In step S303, the control unit 32 measures the pupil diameter based on an image photographed by the observation image sensor 25. The measurement of the pupil diameter is performed by a procedure similar to that performed in step S103 illustrated in FIG. 2.

In step S304, the control unit 32 causes the work memory 37 to store the measured value of the pupil diameter.

In step S305, the control unit 32 increases an amount of light from the target illuminating light source 17 by a preliminarily set amount via the anterior eye observation fixation target light source control unit 35. Subsequently, the control unit 32 waits for a predetermined time.

In step S306, the control unit 32 measures the pupil diameter by performing a procedure similar to that performed in step S303. Subsequently, the control unit 32 detects an amount of change in the pupil diameter by subtracting a measured value of the pupil diameter measured in step S306 from the measured value of the pupil diameter that is stored in the work memory 37 in step S304.

In step S307, the control unit 32 determines whether an amount of change in the pupil diameter, which is acquired in step S306, is less than a threshold. If the amount of change in the pupil diameter is equal to or more than the threshold, the control unit 32 proceeds to step S315.

In step S308, if it is determined based on a result of comparison made in step S307 that the amount of change in the pupil diameter is less than the threshold, the control unit 32 determines whether the amount of light from the target illuminating light source 17 is less than a threshold. If it is determined based on a result of comparison made in step S308 that the amount of light from the target illuminating light source 17 is less than the threshold, the control unit 32 performs processing to be performed in step S305 or later again.

In step S309, if the control unit 32 determines based on a result of the comparison made in step S308 that the amount of light is equal to or more than the threshold, the control unit 32 causes the work memory 37 to store information indicating that mydriatic photographing is being performed, and information representing the amount of change in the pupil diameter acquired in step S306.

In step S310, the control unit 32 performs a control process for moving the filter 3 out of the optical axis L1. A light flux of light for observing the subject's eye E is set by the movement of the filter 3 to be that of visible light. This enables observing a color image of the subject's eye E.

In step S311, the control unit 32 performs a control process for moving the anterior eye observation optical system 12 out of the optical axis L3. This movement of the anterior eye observation optical system 12 changes an image to be formed onto the still image sensor 21 or the observation image sensor 25 from an image of the anterior eye portion $E_p$ of the subject's eye E to an image of the fundus portion $E_r$ thereof.

In step S312, the control unit 32 performs a control process for photographing a fundus image using the photographing light projecting light source 4 upon completion of preparation for photographing.

In step S313, the control unit 32 causes an external storage medium (not shown) to store information representing the photographed image and the information stored in the work memory 37. Incidentally, the file to be stored is similar to that according to the first exemplary embodiment illustrated in FIG. 5.

In step S314, the control unit 32 determines whether all necessary images have been photographed. If there is an image that is not photographed, the control unit 32 performs processing to be performed in step S312 or later again.

In step S315, the control unit 32 notifies, if the control unit 32 determines in step S307 that the amount of change in the pupil diameter is equal to or more than the threshold, that mydriasis of the pupil does not occur. This notification is performed by causing the monitor 39 to indicate a message.

In step S316, the control unit 32 performs, after the processing is performed in step S315, a control process of causing an operator to determine whether the photographing operation is stopped. This control process is performed by causing the monitor 39 to indicate a message. Then, the control unit 32 detects an operation of inputting data corresponding to a specific key, which corresponds to, e.g., a specific letter "Y" or "N", from the keyboard 40. Further, the control unit 32 determines input data represented by the specific key. Thus, the control unit 32 determines whether the photographing operation is stopped or continued. If the operator selects stoppage of the photographing, the photographing operation is stopped. If the operator selects continuation of the photographing, the control unit 32 proceeds to step S311.

Thus, according to the present embodiment, when photographing is performed by the ophthalmologic photographing apparatus, the change in the pupil diameter is measured. Then, the photographing operation can be stopped by notifying, based on the amount of change in the pupil diameter, an operator that the mydriasis of the pupil does not occur. Accordingly, even in a case where an operator forgets to apply a mydriatic to the subject's eye E in the mydriatic photographing mode, the ophthalmologic photographing apparatus can give a warning to the operator before the photographing is performed.

According to the first and second exemplary embodiments, the ophthalmologic photographing apparatus is constructed such that an amount of change in the pupil diameter of the subject's eye E is measured by changing the amount of light from the target illuminating light source 17. However, the control process for changing the amount of light from the target illuminating light source 17 can be eliminated by using, as a light source for changing the amount of light, the observation light source 1 that serves as the observation light projecting unit.

Figure 7:
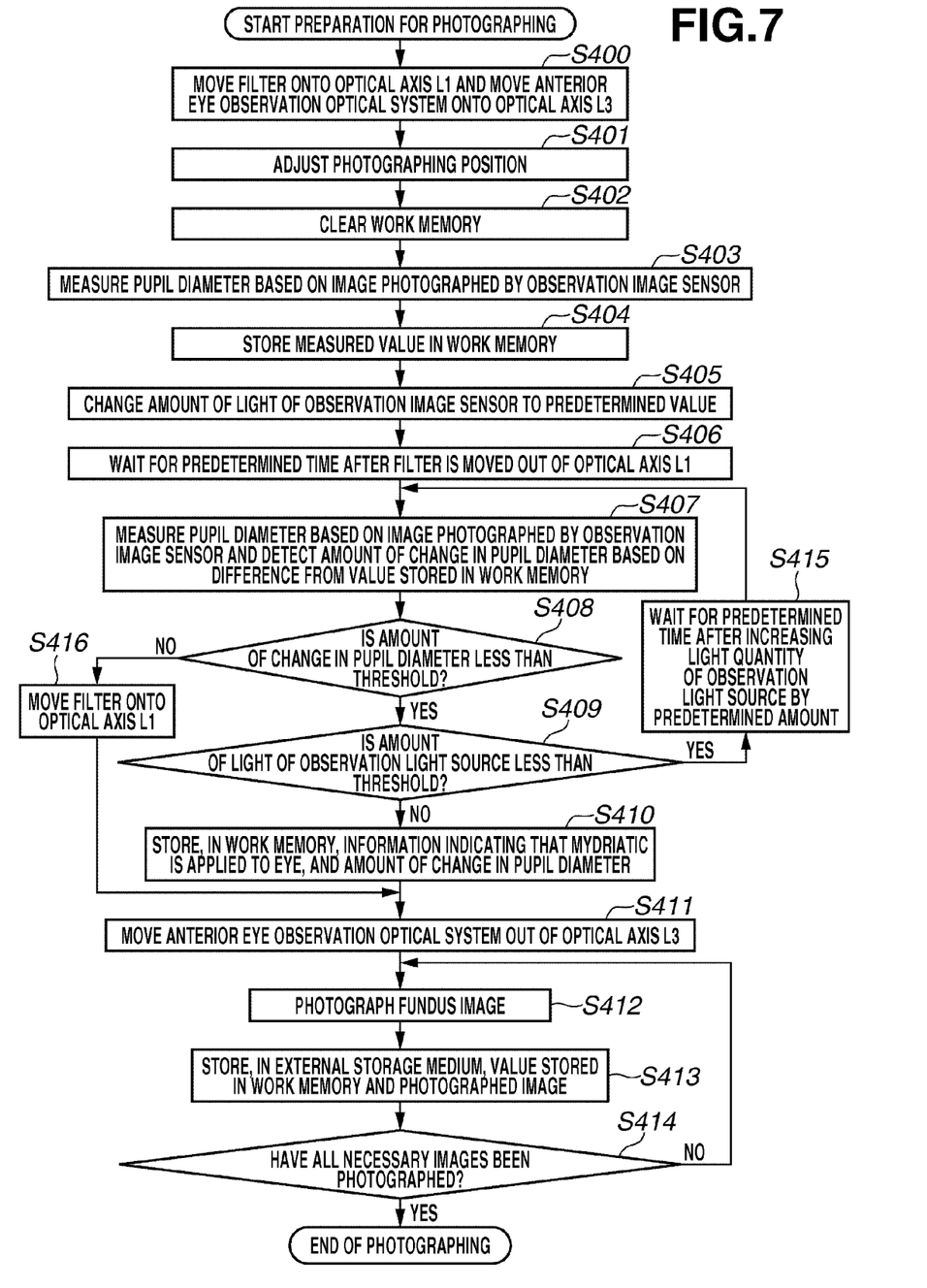
FIG. 7 illustrates a flow of an operation of an ophthalmologic photographing apparatus according to a third exemplary embodiment of the present invention.

FIG. 7 illustrates a flow of an operation of an ophthalmologic photographing apparatus according to a third exemplary embodiment of the present invention, which has a configuration illustrated in FIG. 1 and is adapted to change, based on a change in the amount of light from the observation light source 1, a photographing mode. An operation illustrated in FIG. 7 is performed under the control of the control unit 32 of the ophthalmologic photographing apparatus. Incidentally, processing to be performed in each of steps S400 through S404, and S411 through S414 is similar to that to be performed in associated one of steps S100 through S104, and S111 through S114.

In step S400, if the preparation for photographing is started, the control unit 32 performs a control process for moving the filter 3 onto the optical axis L1. Then, the control unit 32 performs a control process for inserting the anterior eye observation optical system 12 onto the optical axis L3. Thus, infrared light for observing the subject's eye E is projected thereonto. In addition, a photographing position can be adjusted using the anterior eye observation optical system 12.

In step S401, the photographing position is adjusted by an operator. In this case, a fixed value is used as an amount of light from the target illuminating light source 17, without controlling the amount of light. The adjustment of the photographing position is performed by a procedure similar to that performed in step S101 illustrated in FIG. 2.

In step S402, the control unit 32 clears the work memory 37.

In step S403, the control unit 32 measures the pupil diameter based on an image photographed by the observation image sensor 25. The measurement of the pupil diameter is performed by a procedure similar to that performed in step S103 illustrated in FIG. 2.

In step S404, the control unit 32 causes the work memory 37 to store the measured value of the pupil diameter.

In step S405, the control unit 32 increases an amount of the observation light source 1 to a predetermined value.

In step S406, the control unit 32 waits for a predetermined time after the filter 3 is moved out of the optical axis L1. Visible light is projected onto the subject's eye E.

In step S407, the control unit 32 measures the pupil diameter by performing a procedure similar to that performed in step S403. Subsequently, the control unit 32 detects an amount of change in the pupil diameter by subtracting a measured value of the pupil diameter measured in step S407 from the measured value of the pupil diameter that is stored in the work memory 37 in step S404.

In step S408, the control unit 32 determines whether an amount of change in the pupil diameter is less than a threshold. If the amount of change in the pupil diameter is less than the threshold, the control unit 32 proceeds to step S409. If the amount of change in the pupil diameter is not less than the threshold, the control unit 32 proceeds to step S416.

In step S409, the control unit 32 determines whether the amount of light from the observation light source 1 is less than a threshold.

In step S410, if the control unit 32 determines based on a result of the comparison made in step S409 that the amount of light is equal to or more than the threshold, the control unit 32 causes the work memory 37 to store information indicating that a mydriatic is applied to the subject's eye E, and information representing the amount of change in the pupil diameter acquired in step S407.

In step S411, the control unit 32 performs a control process for moving the anterior eye observation optical system 12 out of the optical axis L3. This movement of the anterior eye observation optical system 12 changes an image to be formed onto the still image sensor 21 or the observation image sensor 25 from an image of the anterior eye portion $E_p$ of the subject's eye E to an image of the fundus portion $E_r$ thereof.

In step S412, the control unit 32 performs a control process for photographing a fundus image upon completion of preparation for photographing.

In step S413, the control unit 32 causes an external storage medium (not shown) to store information representing the photographed image and the information stored in the work memory 37 as a file.

In step S414, the control unit 32 determines whether all necessary images have been photographed. If there is an image that is not photographed, the control unit 32 performs processing to be performed in step S412 or later again.

In step S415, if the control unit 32 determines based on a result of comparison made in step S409 that the amount of light from the observation light source 1 is less than the threshold, the control unit 32 waits for a predetermined time after the amount of light from the observation light source 1 is increased to a preliminarily set amount under the control of the control unit 32. Then, the control unit 32 performs processing to be performed in step S407 or later again.

In step S416, if the control unit 32 determines in step S408 that the amount of change in the pupil diameter is equal to or more than the threshold, the control unit 32 performs a control process for moving the filter 3 onto the optical axis L1. Infrared light is projected onto the subject's eye E by moving the filter 3 onto the optical axis L1. Then, the control unit 32 proceeds to step S411. According to the present embodiment, the information displayed on the monitor 39 in the case of selecting and inputting the parameters is similar to that illustrated in FIG. 4.

With the above-described configuration and operation, the process for controlling the amount of light from the target illuminating light source 17 can be eliminated using the observation light source 1 as the light source for changing the amount of light. Consequently, the configuration of the ophthalmologic photographing apparatus can be simplified.

According to the above-described first through third exemplary embodiments, the photographing mode is switched by measuring the pupil diameter before a fundus image is photographed, and the amount of change in the pupil diameter after the fundus image is photographed. However, in order to measure the amount of change in the pupil diameter before a fundus is photographed, there is needed a processing time before the fundus is photographed.

Thus, the ophthalmologic photographing apparatus can be configured such that the photographing mode is switched by measuring the pupil diameter before the fundus image is photographed and the change in the pupil diameter after the fundus image is photographed.

Figure 8:
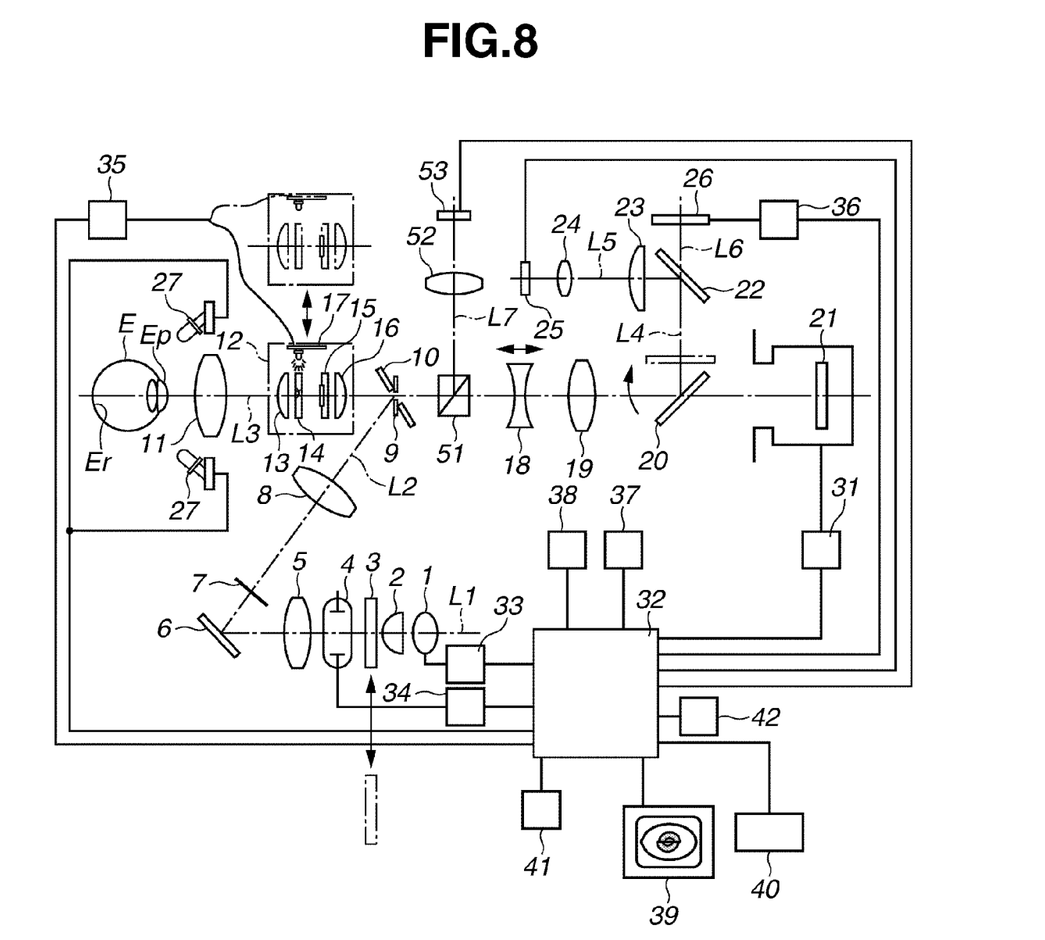
FIG. 8 illustrates a configuration of an ophthalmologic photographing apparatus according to a fourth exemplary embodiment of the present invention.

FIG. 8 illustrates a configuration of an ophthalmologic photographing apparatus according to a fourth exemplary embodiment of the present invention, in which an optical system is added to the ophthalmologic photographing apparatus according to the first through third exemplary embodiments so as to be able to measure both of the pupil diameter before the fundus image is photographed and the change in the pupil diameter after the fundus image is photographed. That is, a prism 51 is located on the optical axis L3 between the perforated mirror 10 and the focusing lens 18. A lens 52 and an anterior eye observation image sensor 53 connected to the control unit 32 are located on an optical axis L7, which is formed by the prism 51.

The anterior eye observation image sensor 53 is located so as to be substantially conjugated with the anterior eye portion $E_p$ of the subject's eye E with respect to the objective lens 11 and the lens 52 when an operating distance between the subject's eye E and the objective lens 11 is appropriate.

Figure 9:
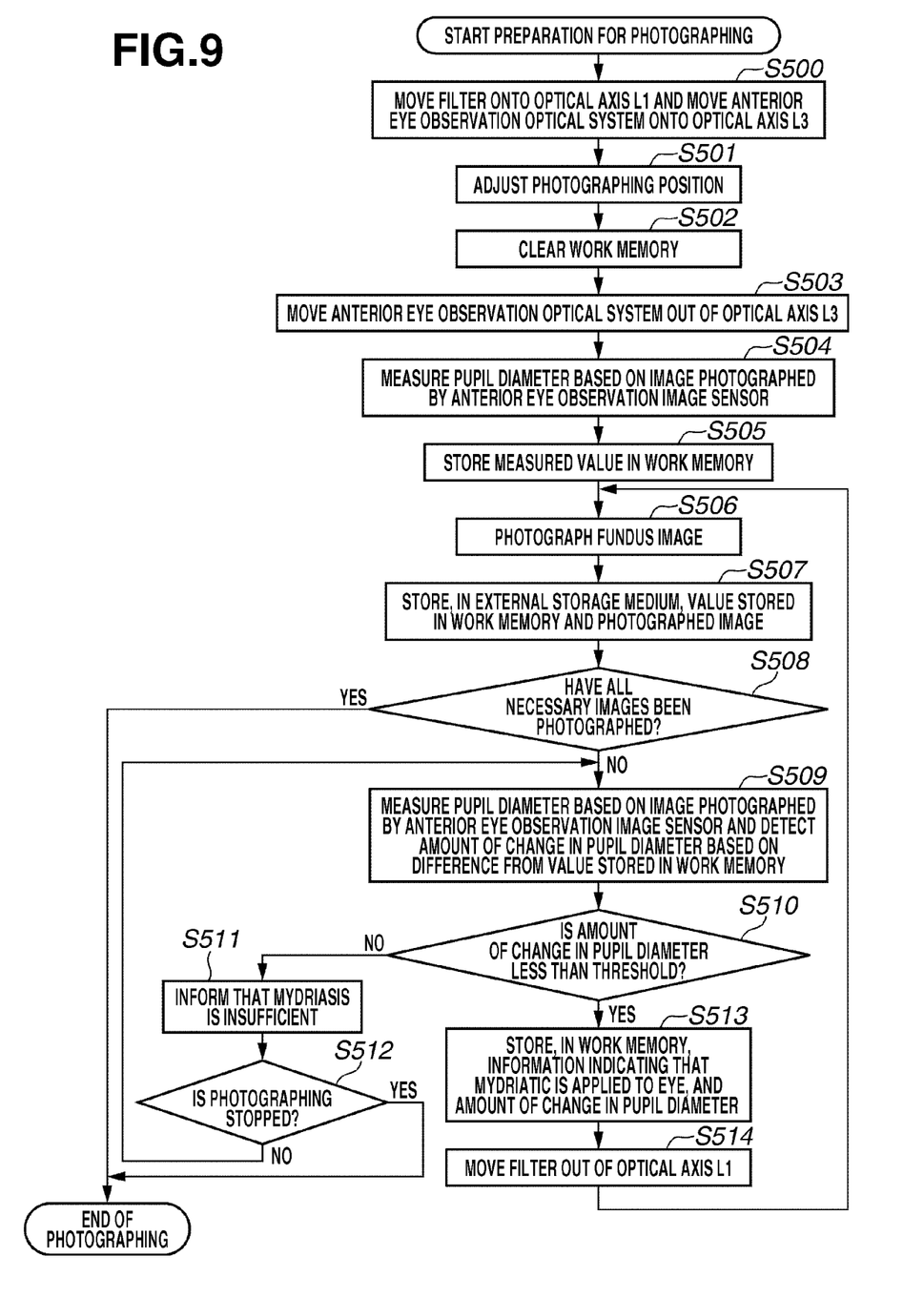
FIG. 9 illustrates a flow of an operation of the ophthalmologic photographing apparatus according to the fourth exemplary embodiment of the present invention.

FIG. 9 illustrates a flow of an operation of switching, based on the amount of change in the pupil diameter, a method for photographing a fundus image using a fundus camera. An operation illustrated in FIG. 9 is performed under the control of the control unit 32 of the ophthalmologic photographing apparatus.

In step S500, if the preparation for photographing is started, the control unit 32 performs a control process for moving the filter 3 onto the optical axis L1. Then, the control unit 32 performs a control process for inserting the anterior eye observation optical system 12 onto the optical axis L3. Thus, infrared light for observing the subject's eye E is projected thereonto. In addition, a photographing position can be adjusted using the anterior eye observation optical system 12.

In step S501, the control unit 32 performs a control process for adjusting the photographing position. The adjustment of the photographing position is performed by a procedure similar to that performed in step S101 illustrated in FIG. 2.

In step S502, the control unit 32 clears the work memory 37.

In step S503, the control unit 32 performs a control process for moving the anterior eye observation optical system 12 out of the optical axis L3. This movement of the anterior eye observation optical system 12 changes an image to be formed onto the still image sensor 21 or the observation image sensor 25 from an image of the anterior eye portion $E_p$ of the subject's eye E to an image of the fundus portion $E_r$ thereof. With this operation, a fundus image can be photographed. In addition, an image of the anterior eye portion $E_p$ of the subject's eye E is formed on the anterior eye observation image sensor 53.

In step S504, the control unit 32 measures the pupil diameter based on an image of the anterior eye portion $E_p$ of the subject's eye E photographed by the anterior eye observation image sensor 53. The measurement of the pupil diameter is performed by a procedure similar to that performed in step S103 illustrated in FIG. 2.

In step S505, the control unit 32 causes the work memory 37 to store the measured value of the pupil diameter. Thus, the preparation for photographing is completed.

In step S506, the control unit 32 performs fundus image photographing upon completion of preparation for photographing.

In step S507, the control unit 32 causes an external storage medium (not shown) to store information representing the photographed image and the information stored in the work memory 37 as a file.

In step S508, the control unit 32 determines whether all necessary images have been photographed. If there is no image that is not photographed, photographing is finished.

In step S509, if there is an image that is not photographed, the control unit 32 measures a pupil diameter by a procedure similar to that performed in step S504. Then, the control unit 32 detects an amount of change in the pupil diameter by subtracting a measured value of the pupil diameter measured in step S509 from the measured value of the pupil diameter stored in the work memory 37 in step S505.

In step S510, the control unit 32 determines whether the amount of change in the pupil diameter, which is acquired in step S509, is less than a threshold.

In step S511, the control unit 32 notifies, if the control unit 32 determines in step S510 that the amount of change in the pupil diameter is equal to or more than the threshold, that mydriasis of the pupil is insufficient. This notification is performed by indicating a message on the monitor 39.

In step S512, the control unit 32 performs a control process for causing an operator to determine whether the photographing operation is stopped. Then, the control unit 32 causes the monitor 39 to display a message. Simultaneously, the control unit 32 detects an operation of inputting data corresponding to a specific key, which corresponds to, e.g., a specific letter "Y" or "N", from the keyboard 40. If the control unit 32 detects data representing stoppage of photographing, the control unit 32 stops a photographing operation. If the control unit 32 detects data representing continuation of photographing, the control unit 32 performs processing to be performed in step S509 or later again.

In step S513, if the control unit 32 determines, based on a result of comparison made in step S510, that the amount of change in the pupil diameter is less than the threshold, the control unit 32 causes the work memory 37 to store both of information indicating that a mydriatic is applied to the subject's eye E and information representing an amount of change in the pupil diameter, which is acquired in step S509.

In step S514, the control unit 32 performs a control process for moving the filter 3 out of the optical axis L1. Then, the control unit 32 performs processing to be performed in step S509 or later again. Visible light is projected onto the subject's eye E by moving the filter 3 out of the optical axis L1. Consequently, a color image of the fundus portion $E_r$ Of the subject's eye E can be observed.

According to the above-described configurations and operations, the ophthalmologic photographing apparatus is constructed to use the photographing light projecting light source 4 and to measure the amount of change in the pupil diameter between a state before photographing is performed and a state after photographing is performed. This eliminates the necessity for measuring an amount of change in the pupil diameter before a fundus image is photographed. Consequently, a time taken to enable photographing a fundus image can be shortened.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-096815 filed Apr. 3, 2008, which is hereby incorporated by reference herein in its entirety.

What is claimed is:

1. An ophthalmologic apparatus comprising:
    a light projecting unit configured to project visible light to a subject's eye;
    a detection unit configured to detect an amount of a change in pupil size for the subject's eye which is caused by the visible light from the light projecting unit; and
    a notification unit configured to notify an operator of the ophthalmologic apparatus that mydriasis of the subject's eye is insufficient in a case where the detected amount of change is equal to or more than a threshold.

2. A control method implemented in an ophthalmologic apparatus which includes a light projecting unit configured to project visible light to a subject's eye, the control method comprising:
    detecting an amount of a change in pupil size for the subject's eye which is caused by the visible light from the light projecting unit; and
    notifying an operator of the ophthalmologic apparatus that mydriasis of the subject's eye is insufficient in a case where the detected amount of change is equal to or more than a threshold.

3. A non-transitory computer-readable medium having stored thereon a program for performing a method according to claim 2.

4. The ophthalmologic apparatus according to claim 1 further comprising:
    a determining unit configured to determine whether to either stop or continue photographing the subject's eye based on the amount of the change in pupil size.

5. The ophthalmologic apparatus according to claim 4, wherein the determining unit determines whether to stop photographing the subject's eye in a case where the amount of the change in pupil size is not less than a predetermined value.

6. The ophthalmologic apparatus according to claim 4, wherein the determining unit determines whether to continue photographing the subject's eye in a case where the amount of the change in pupil size is less than a predetermined value.

* * * * *